United States Patent
Kouyoumjian et al.

(10) Patent No.: US 9,750,890 B2
(45) Date of Patent: Sep. 5, 2017

(54) MECHANISM FOR A DRUG DELIVERY DEVICE

(75) Inventors: Garen Kouyoumjian, Leamington Spa (GB); Robert Veasey, Leamington Spa (GB); David Plumptre, Droitwich Spa (GB); Christopher Jones, Tewkesbury (GB); Catherine Anne Macdonald, Ashby-de-la-Zouch (GB); Matthew Jones, Warwick (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1339 days.

(21) Appl. No.: 13/496,537

(22) PCT Filed: Sep. 29, 2010

(86) PCT No.: PCT/EP2010/064406
§ 371 (c)(1),
(2), (4) Date: Jul. 24, 2012

(87) PCT Pub. No.: WO2011/039215
PCT Pub. Date: Apr. 7, 2011

(65) Prior Publication Data
US 2012/0283657 A1    Nov. 8, 2012

(30) Foreign Application Priority Data
Sep. 30, 2009 (EP) ..................... 09171747

(51) Int. Cl.
*A61M 5/00* (2006.01)
*A61M 5/315* (2006.01)
(Continued)

(52) U.S. Cl.
CPC .......... *A61M 5/31585* (2013.01); *A61M 5/24* (2013.01); *A61M 5/3158* (2013.01);
(Continued)

(58) Field of Classification Search
CPC ............ A61M 5/3158; A61M 5/31551; A61M 5/315; A61M 5/31585; A61M 5/3155
(Continued)

(56) References Cited

U.S. PATENT DOCUMENTS 1,997,129 A * 4/1935 Taylor ....................... F16N 3/08
222/309
4,973,318 A * 11/1990 Holm ...................... A61M 5/24
604/208
(Continued)

FOREIGN PATENT DOCUMENTS

EP 0058536 8/1982
JP 2007-509662 4/2007
(Continued)

OTHER PUBLICATIONS

European Search Report for App. No. EP 13185061, completed Oct. 7, 2013.
(Continued)

Primary Examiner — Phillip Gray
(74) Attorney, Agent, or Firm — McDonnell Boehnen Hulbert & Berghoff LLP (57) ABSTRACT

The present invention relates to an assembly forming a piston rod for advancing a cartridge bung in a drug delivery device, the assembly comprising a first member and a second member wherein in a first state, the first and the second member are moveable with respect to each other to adjust the length of the piston rod and wherein in a second state the first member is locked in position with respect to the second member in order to define a fixed length of the piston rod. Furthermore, it relates to a drug delivery device comprising the assembly and to a method for assembling such a drug delivery device.

13 Claims, 4 Drawing Sheets (51) Int. Cl.
*A61M 5/24* (2006.01)
*A61M 5/31* (2006.01)

(52) U.S. Cl.
CPC ....... *A61M 5/31555* (2013.01); *A61M 5/3146* (2013.01); *A61M 2005/2407* (2013.01); *A61M 2205/6081* (2013.01); *A61M 2207/00* (2013.01); *Y10T 29/49826* (2015.01)

(58) Field of Classification Search
USPC .......................................... 604/206–211, 127
See application file for complete search history.

(56) References Cited

U.S. PATENT DOCUMENTS

| | | |
|---|---|---|
| 6,241,709 B1 | 6/2001 | Bechtold et al. |
| 2005/0222540 A1 | 10/2005 | Kirchhofer et al. |
| 2006/0229570 A1 | 10/2006 | Lovell et al. |
| 2006/0258988 A1 | 11/2006 | Keitel et al. |
| 2008/0071226 A1 | 3/2008 | Moser et al. |
| 2008/0208144 A1 | 8/2008 | Moller |

FOREIGN PATENT DOCUMENTS

| | | |
|---|---|---|
| WO | 03/099357 | 12/2003 |
| WO | 2009/108869 | 9/2009 |

OTHER PUBLICATIONS

European Search Report for EP App. No. 09171747, completed Mar. 15, 2010.
International Search Report for International App. No. PCT/EP2010/064406, completed Jan. 27, 2011.
International Preliminary Report on Patentability for International App. No. PCT/EP2010/064406, completed Jan. 1, 2012.
English translation of Japanese Office Action for JP App. No. 2012-531383, mailed Aug. 5, 2014.

\* cited by examiner

MECHANISM FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2010/064406 filed Sep. 29, 2010, which claims priority to European Patent Application No. 09171747.0 filed on Sep. 30, 2009. The entire disclosure contents of these applications are herewith incorporated by reference into the present application.

FIELD OF INVENTION

The present invention relates to an assembly for use in a drug delivery device.

BACKGROUND

Drug delivery devices are generally known for the administration of a medicinal product, for example insulin or heparin, but also for other medicinal products for self-administration by a patient. Most of the drug delivery devices are pen-type injectors, which dispense a pre-set dose of a fluid medicinal product.

Document EP 0 058 536 A1 shows an example for a drug delivery device where a pre-set dose can be administered. For dispensing the dose, a plunger is screwed with respect to a fixed sleeve, thereby advancing a plug in a fluid containing cylinder.

Before the first use of the drug delivery device the user usually has to prime the drug delivery device. Users who are unfamiliar with such pen-type injectors may fail or incorrectly prime their drug delivery device before dispensing the first dose.

SUMMARY

It is an object to the present disclosure to provide an assembly for use in a drug delivery device, which helps to improve usability and ensures the accuracy of the first dispensed dose of a fluid medicinal product.

According to a first aspect of the present disclosure, an assembly is provided, which is forming a piston rod for advancing a cartridge bung in a drug delivery device. The assembly comprises a first member and a second member. In a first state of the assembly, the first and the second member are moveable with respect to each other to adjust the length of the piston rod. In a second state of the assembly, the first member is locked in position with respect to the second member in order to define a fixed length of the piston rod. In the second state of the assembly, i.e. when the length of the piston rod is fixed, the assembly may be set-up and may be used by a patient for the application of a medicament, which may comprise setting and dispensing a dose of a medicinal product. In this state, the operation of the device may be performed only once or also repeatedly. In the first state, the assembly is used for preparative purposes only and is not suited for a set and dispense action.

After the piston rod is formed in the second state, the drug delivery device can be used without the requirement for a priming dose to prepare the device first.

For fixed dose devices the dose setting may include the step of loading the device whereas afterwards dispensing a predefined amount of medication is performed, whereas in the case of a variable dose device the step of setting includes the adjustment of the device to define the amount of medication to be dispensed in the subsequent dispensing operation.

By means of the adjustment of the length of the piston rod, tolerances of the mechanical elements are removed from the assembly. Additionally, the need for a priming operation before delivering the first dose can be avoided. Thereby, one advantage is that the user will not accidentally inject prime fluid.

This arrangement may be used for fixed dose pens as well as for variable dose pens.

The second member may comprise ratchet teeth or a lead screw as part of the related drive mechanism. In case of a ratchet teeth based drive mechanism, the piston rod is linearly advanced and in case of a lead screw based drive mechanism, the piston rod is rotationally advanced.

In a preferred embodiment in the first state of the assembly, the first member is coupled to an adjustment member such that relative axial movement between the first member and the adjustment member is permitted and rotational movement relative to each other is prevented.

The first member may comprise a part, which has a non-circular cross section. The adjustment member may comprise an aperture through which the part of the first member, which has a non-circular cross section, can extend. The shape of the non-circular cross section of the first member and the shape of the aperture of the adjustment member match such that relative axial movement between the first member and the adjustment member is permitted and relative rotational movement is prevented.

The assembly comprises a distal end, where the medicinal product may be dispensed out of an assembled medicament cartridge and a proximal end, which indicates the end opposite to the distal end.

The first member may be located within a bore along the longitudinal axis of the second member and extends beyond the proximal end of the second member. The adjustment member may control the rotational movement of the first member through the second member. Additionally, the location of the first member with respect to the second member may be locked by means of the adjustment member.

In another preferred embodiment, the assembly comprises a threaded engagement between the first member and the second member.

The first member may comprise an external thread, which engages with an internal thread of the distal end of the second member. The adjustment member is rotatable relative to the second member. Preferably, the adjustment is intended to be undertaken during assembly of the device in the factory. Consequently, the rotation of the adjustment member may be performed by a machine. As a consequence of the rotational movement of the adjustment member, the first member is advanced through the second member.

In a particularly preferred embodiment, the threaded engagement is self-locking.

The pitch of the threads at the first and at the second member may be chosen such that the threaded engagement is self-locking. This means that an axial displacement can not result in a rotational movement because of the low pitch and the dynamic friction between the engaged threads. Due to the self-locking threaded engagement, it is not necessary to lock the first member with the second member at the proximal end.

According to another preferred embodiment, the first member is at least partly arranged inside the second member.

The first member may protrude from the distal end and from the proximal end of the second member.

In another preferred embodiment, the adjustment member is arranged such that a rotational movement of the adjustment member relative to the second member advances the first member axially relative to the second member.

In this case, the adjustment member is connected to the first member such that rotating the adjustment member advances the first member through the second member.

In a particular preferred embodiment, the first member comprises a pad configured to abut an assembled cartridge bung while being advanced relative to the second member.

At the distal end of the first member, the first member may comprise a pad that protrudes from the second member and may abut a proximal face of a cartridge bung. By advancing the piston rod, the pad applies a pressure onto the cartridge bung, thereby pushing the cartridge bung in distal direction. The movement of the cartridge bung expels a fluid medicinal product out of an assembled medicament cartridge.

In addition, a bearing might be located at the distal end of the first member, which can abut a proximal face of a cartridge bung. The bearing might be arranged such that relative rotation between the parts is permitted but relative axial movement is not permitted.

The bearing might be useful in the case that the piston rod rotates during the dispense of a dose of a fluid medicinal product. The rotational movement leads to a torque, which is absorbed by the bearing such that the bung is only axially displaced.

In another particular preferred embodiment, the advancing movement of the first member relative to the second member is stopped when the pad contacts the cartridge bung.

Before the first use of the drug delivery device, there is typically a gap between the end of the piston rod and the cartridge bung. This gap is a consequence of the tolerances associated with all the assembled parts and the requirement not to pre-load the bung axially in the assembled device. The gap is closed by the pad, which is advanced into contact with the cartridge bung through its axial motion relative to the second member.

After closing the gap between the pad and the cartridge bung properly, the correct volume of a medicinal product may be delivered in the first dispensed dose.

According to another particular preferred embodiment, the assembly comprises a means to detect the abutment of the pad upon the bung and to stop the movement of the first member.

The abutment of the pad and a proximal face of the bung can be detected for example by a strain gauge to measure torque and give according feedback, which at a predetermined level indicates contact between the pad and the cartridge bung. Another possibility to detect the abutment of the pad and the cartridge bung is for example by using a clutch that is designed to slip at a certain torque value.

In a preferred embodiment, in a second state of the assembly, the first member and the second member are suitable for moving the cartridge bung into an assembled medicament cartridge for dispensing a fluid medicinal product.

After having connected the first member with the second member a piston rod is formed. The piston rod may be advanced by means of a drive mechanism. The advancing piston rod may move a cartridge bung in an assembled medicament cartridge. Due to the advancing cartridge bung, a fluid medicinal product is dispensed from the medicament cartridge.

In another preferred embodiment, the adjustment member is located at the distal end of the assembly.

In one preferred embodiment in the second state of the assembly the adjustment member is locked with the second member in order to prevent rotational and axial movement with respect to the second member.

A set of teeth on the distal end of the adjustment member may be disposed towards another set of teeth on the proximal end of the second member. The adjustment member in the first state is, for example mounted on a proximal detent of the second member, such that the opposing sets of teeth are not engaged. In the second state, the sets of teeth between the two parts engage, thus locking them to prevent relative rotation.

In another preferred embodiment, in the second state of the assembly, the adjustment member is connected to the first member such that relative rotation and axial displacement between the adjustment member and the first member is prevented.

Thus, the first member and the second member are forming the piston rod due to the rigid connection.

In a third aspect of the present disclosure, a method for assembling a drug delivery device is provided, wherein the drug delivery device comprises a body, a piston rod and a cartridge holder in which a medicament cartridge is located. The medicament cartridge comprises a bung. An adjustment member and a pad located at the distal end of the first member are moved with respect to a second member until the pad is abutting the cartridge bung of the medicament cartridge. The first member is coupled with the second member such that further movement between the first member and the second member is prevented whereby the piston rod is formed.

An alternative method of the final assembly could be that a medicament cartridge is placed into the cartridge holder and biased in its most distal position. The position of the cartridge bung is then measured. The position of the distal end of the first member or, if applicable, the position of the bearing within the device mechanism is also measured and the required position of the first member relative to the body is calculated, such that when the two sub-assemblies are connected together, there is no gap or excessive pre-load between the end of the first member and the cartridge bung. The first member is adjusted relative to the second member and locked in the position defined by the calculation during assembly of the device.

The terms "medicinal product", "fluid medicinal product" and "medicament" as used herein, preferably mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(0)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(0)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

In the following, the disclosed devices and methods are described in further details with reference to the drawings, wherein.

DETAILED DESCRIPTION

Some preferred embodiments of the arrangement according to the present disclosure will now be discussed with reference to FIG. 1, FIGS. 2a and 2b, FIG. 3 and FIGS. 4a and 4b. Identical reference signs denote identical or comparable components.

Figure 1:
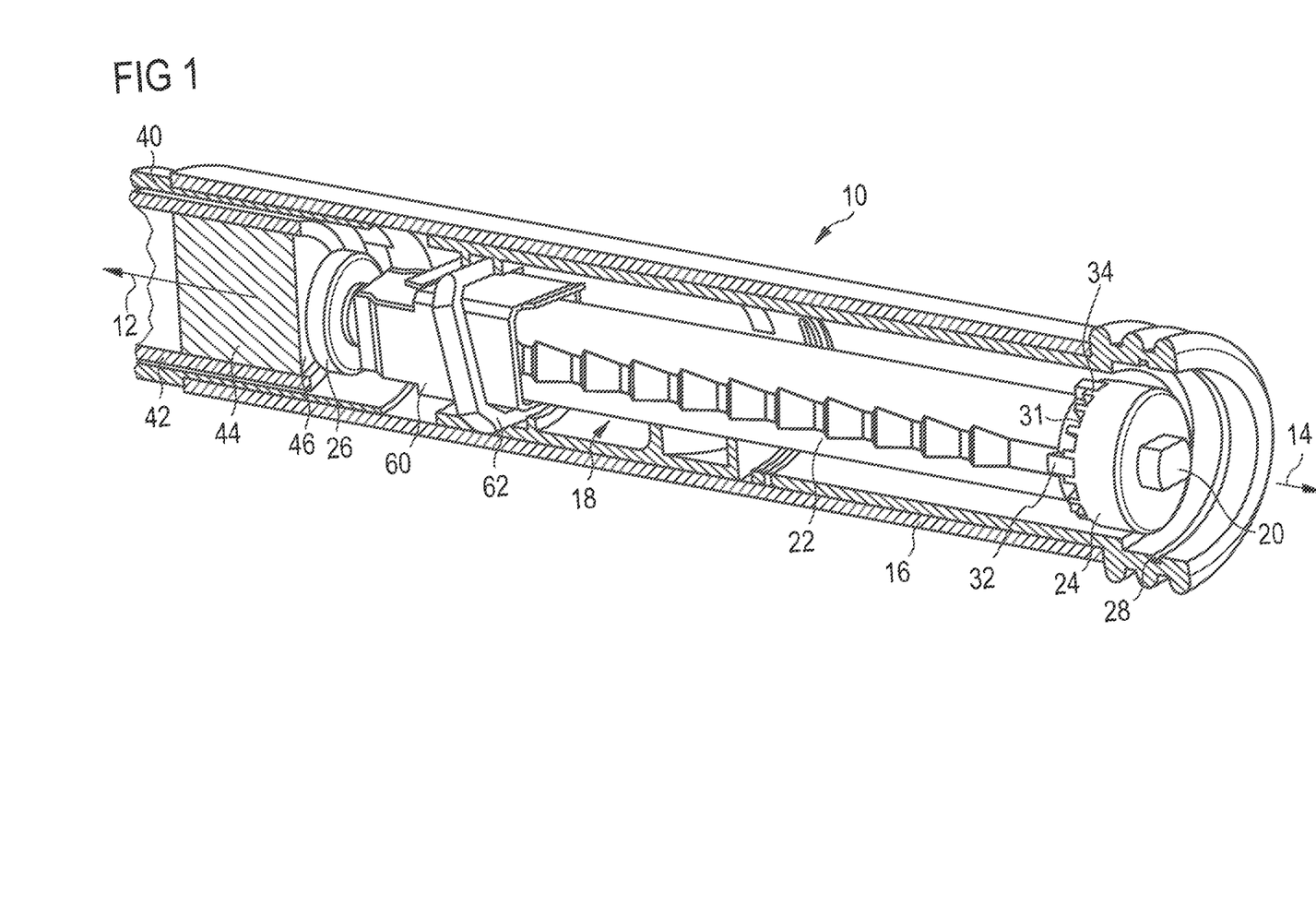
FIG. 1 shows a cut-away view of a drug delivery device comprising a second member, wherein the second member comprises ratchet teeth.

FIG. 1 shows a three-dimensional cut-away view of a first embodiment of the present disclosure.

The drug delivery device 10 comprises a body 16 and a cartridge holder 40. A medicament cartridge 42 is located within the cartridge holder 40. The medicament cartridge 42 contains a number of doses of a fluid medicinal product. During use, the cartridge holder 40 is attached to the body 16 of the drug delivery device 10.

The assembly is located substantially within the body 16 of the drug delivery device 10. The second member 22 is arranged on the main axis of the drug delivery device 10 and is initially located almost entirely within the body 16. The second member 22 is essentially tubular in shape, having a bore that extends completely through its main axis.

At the distal end of the bore, the second member 22 comprises an internal thread. At the proximal end, the second member 22 comprises a set of teeth 32.

The first member 20 is located within the bore of the second member 22 and comprises an external thread, which engages with the internal thread at the distal end of the second member 22. At the extreme distal end of the first member 20 a pad 26 is located that is disposed to abut the proximal face 46 of the cartridge bung 44, while the drug delivery device 10 is operated by a user.

At the proximal end, the first member 20 comprises a part at its proximal end, which has a non-circular cross section. This part of the first member 20 extends beyond the proximal end of the second member 22. The non-circular shaped part of the first member 20 extends through an aperture in the adjusting member 24 such that axial movement between the first member 20 and the adjustment member 24 is permitted, whilst relative rotational movement is not permitted.

The adjustment member 24 has a set of teeth 34 on its distal face, disposed towards the teeth 32 on the proximal end of the second member 22. The adjustment member 24 is initially mounted on a proximal detent, which is not explicitly shown, located at the second member 22, such that opposing sets of teeth are not engaged.

When mounted on this detent, relative rotation between the adjustment member 24 and the second member 22 is permitted but accidental engagement between the opposing sets of teeth is prevented.

During use, the piston rod formed by the first member 20 and the second member 22 is advanced by means of the lever 62 and carrier plate 60 to displace the cartridge bung 44 and to deliver doses of the fluid medicinal product.

Figure 2A:
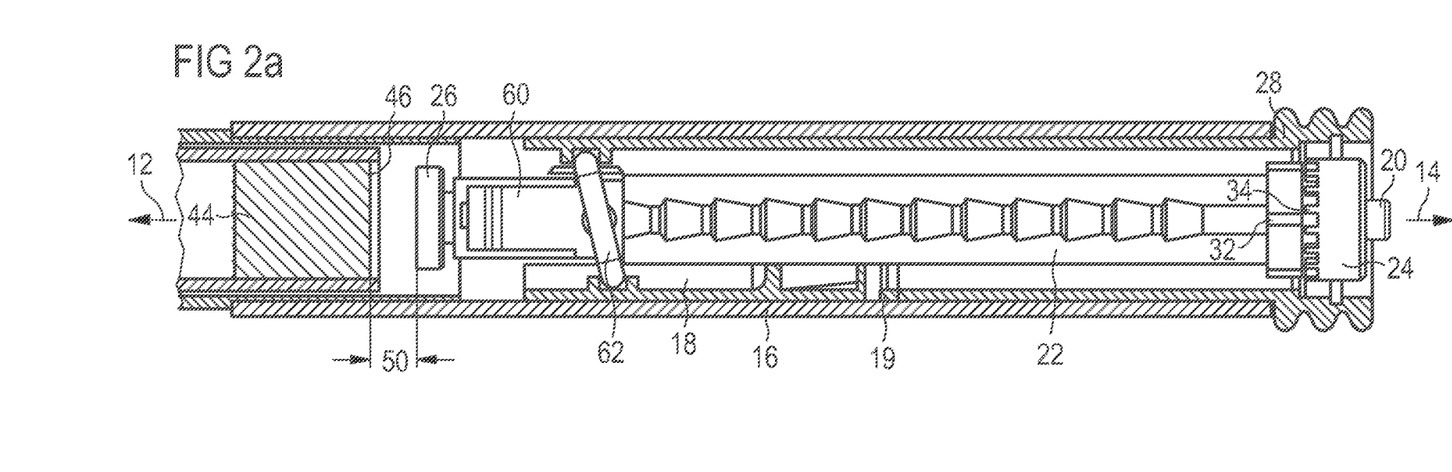
FIG. 2a shows a section view before adjusting the drug delivery device, wherein the drug delivery device comprises a second member and the second member comprises ratchet teeth.

FIG. 2a shows the drug delivery device in a section view before the adjustment.

During the final assembly, a medicament cartridge 42 is first placed into the cartridge holder 40 and the cartridge holder 40 is then connected to the body 16. A gap 50 is shown between the pad 26 and the proximal face 46 of the cartridge bung 44. The assembly is then adjusted such that the gap 50 between the pad 26 at the extreme distal end of the first member 20 and the cartridge bung 44 is removed.

The dose member 28 is first displaced in the distal direction 12 until it engages a stop face 19 on the fixed member 18. This step is important to ensure that all mechanism tolerances are correctly taken up and that a back off spring, which is not shown, is compressed.

The adjustment member 24 is then rotated relative to the second member 22. This action advances the first member 20 through the internal thread of the second member 22. The first member 20 is rotated until it abuts the proximal end face 46 of the cartridge bung 44.

A distal detent, which is not explicitly shown, is located at the second member 22. When the adjustment member 24 is pushed in distal direction 12, it is thereby being pushed onto the distal detent on the second member 22. This action now engages the sets of teeth between the second member 22 and the adjustment member 24, thus locking them to prevent relative rotation, thereby forming the piston rod. The distal detent prevents the axial disengagement of the opposing sets of teeth.

Figure 2B:
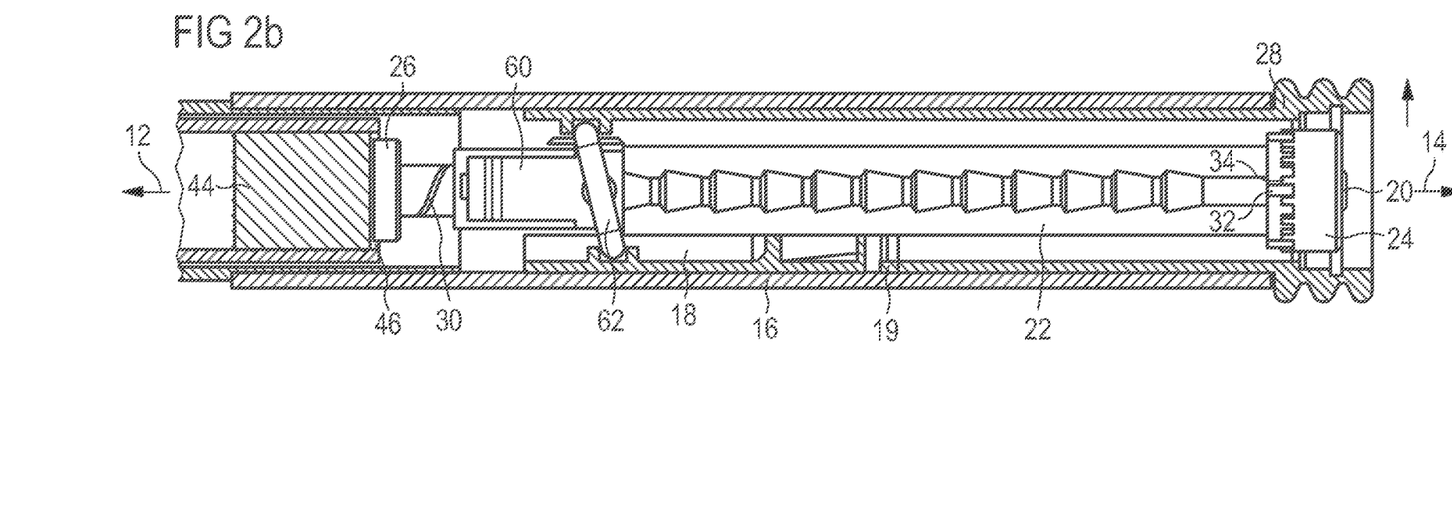
FIG. 2b shows a section view after adjusting the drug delivery device, wherein the drug delivery device comprises a second member and the second member comprises ratchet teeth.

Since the aperture of the adjustment member 24 remains engaged with the non-circular cross section of the first member 20, the first member 20 is now locked in position relative to the second member 22. This is shown in FIG. 2b.

The assembly can then be sealed by the addition of a cap, which is not shown, into the aperture at the proximal end of the dose member 28. This cap can be used to code the drug delivery device 10 by means of color or tactile features, to indicate the type of fluid medicinal product contained therein.

During use, the piston rod formed by the first member 20 and the second member 22 is advanced by means of the lever 62 and carrier plate 60 to displace the cartridge bung 44 and to deliver doses of fluid medicinal product.

One part of the lever 62 is engaged with the fixed member 18 and another part of the lever 62 is connected to the dose member 28. For setting a dose of the fluid medicinal product, the dose member 28 moves proximally with respect to the body 16, thereby moving the lever 62 proximally with respect to the piston rod.

For dispensing a dose of the fluid medicinal product, the dose member 28 is moved in distal direction, whereby the lever 62 and the piston rod are displaced towards the distal end of the drug delivery device. The distal movement of the piston rod displaces the cartridge bung 44 to deliver a dose of a fluid medicinal product.

Figure 3:
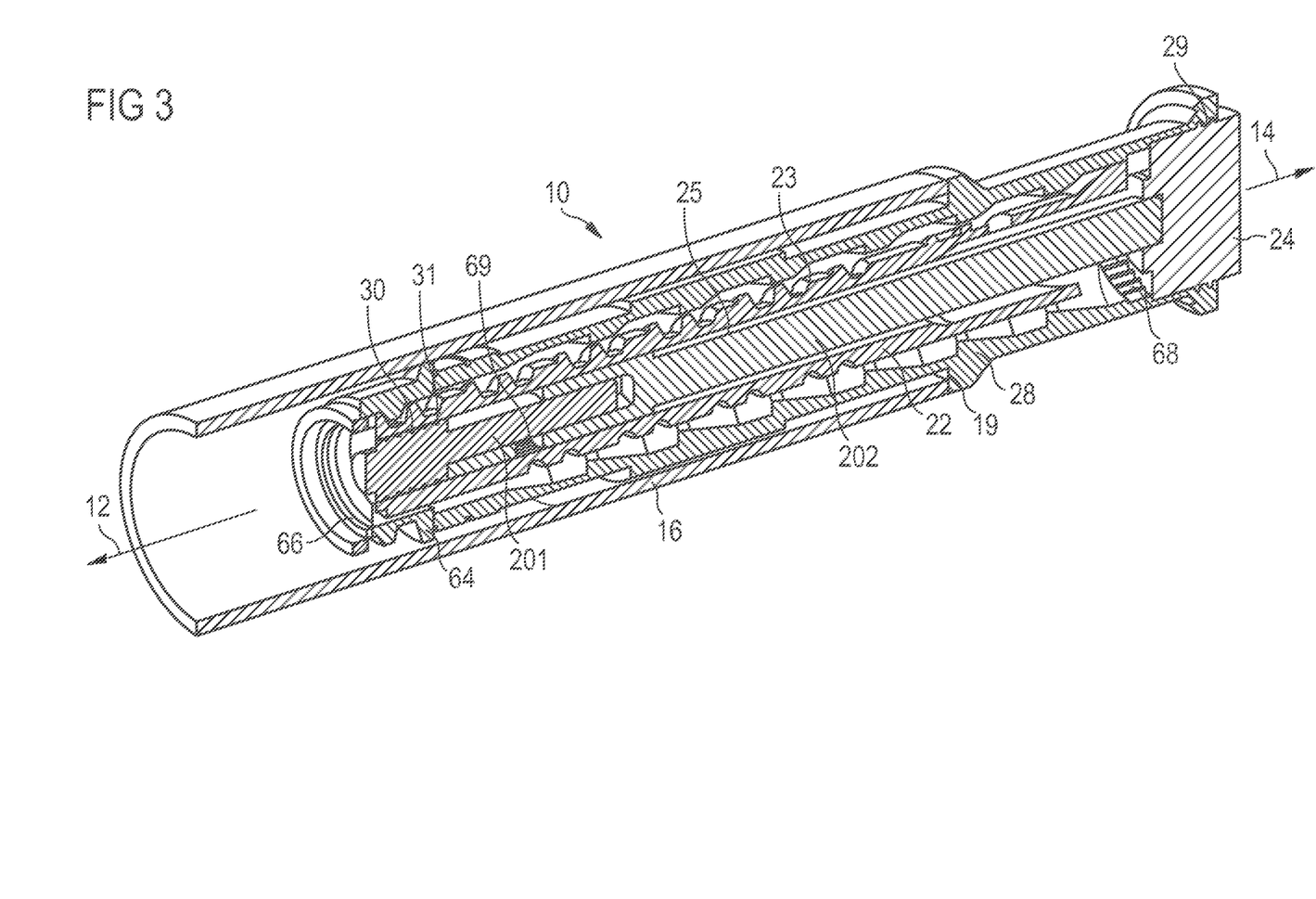
FIG. 3 shows a cut-away view of a drug delivery device comprising a second member, wherein the second member comprises a lead screw.

FIG. 3 shows a three-dimensional cut-away view of a second embodiment of the assembly. In this embodiment, the second member 22 comprises a lead screw and the first member is split up into two parts, a distal part 201 and a proximal part 202.

Similar to FIG. 1, the drug delivery device comprises two parts, a body 16 and a cartridge holder 40. Within the cartridge holder, a medicament cartridge 42 is located, which contains a number of doses of fluid medicinal product. During use, the cartridge holder is permanently attached to the body 16 of the drug delivery device.

The assembly is located substantially within the body 16 of the drug delivery device. The second member 22 lies on the main axis of the pen-type injector and is initially located almost entirely within the body. The second member 22 is essentially tubular in shape with helical thread forms 23 on external surfaces and a bore 25 that extends completely through the main axis.

At the distal end of the bore 23, the second member 22 has an internal thread 31. Adjacent to the internal thread 31 within the bore 23 of the second member 22 a set of spline features 69 is arranged circularly around the internal surface of the bore 23. Proximally behind these spline features 69, two detents are located, which are not explicitly shown.

A first member is located within the bore 23 of the second member 22. The distal part 201 of the first member comprises an external thread 30, which engages with the internal thread 31 at the distal end of the second member 22. At the extreme distal end 201 of the first member, the first member is connected to a bearing 66 by means of a journal that allows relative rotation between the parts but not axial movement. In use, the bearing 66 is disposed to abut the proximal face of the cartridge bung.

At its proximal end, the distal part 201 of the first member comprises a part which has a non-circular cross section. This part comprising the non-circular cross section extends into a distal aperture of a proximal part 202 of the first member, such that limited relative axial movement between the two parts is permitted, whilst relative rotational movement is not.

The proximal part 202 of the first member is initially mounted in a detent of the second member 22, which is not explicitly shown, such that the spline features 69 are not engaged with the opposing set of spline features on the second member 22. When mounted on this detent, relative rotation between the proximal part 202 of the first member and the second member 22 is permitted.

The adjustment member 24 is then mounted in a proximal detent 29 on the dose member 28, such that spline features 68 are not engaged with a set of opposing spline features on an internal cylindrical surface of the dose member 28.

Figure 4A:
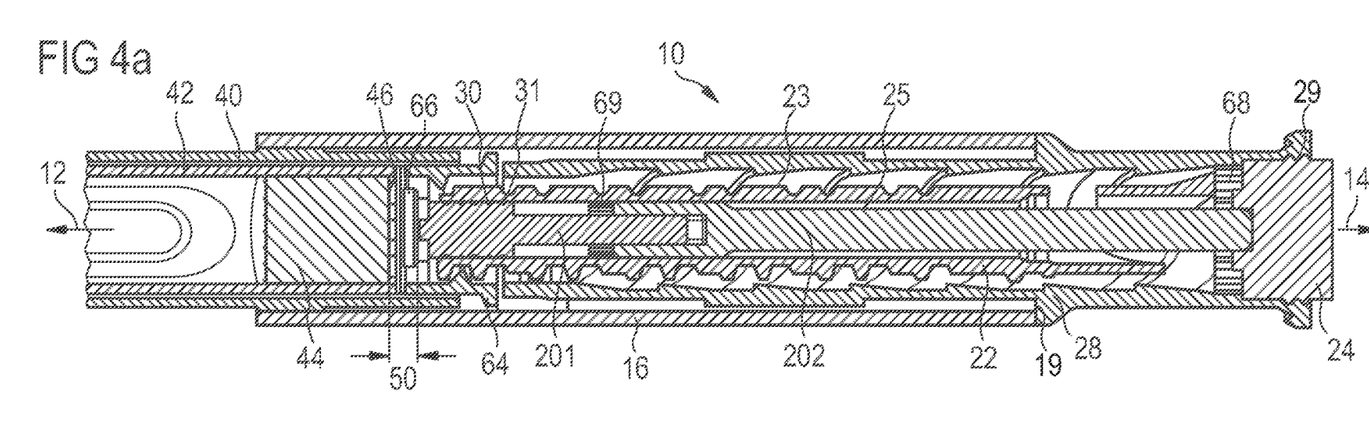
FIG. 4a shows a section view before adjusting the drug delivery device, wherein the drug delivery device comprises a second member and the second member comprises a lead screw.

FIG. 4a shows the drug delivery device in a section view before the adjustment similar as shown in FIG. 3.

During final assembly, a medicament cartridge 42 is first placed into the cartridge holder 40 and the cartridge holder 40 is then connected to the body 16. There is a gap 50 between the bearing 66 and the proximal face 46 of the cartridge bung 44. The assembly is then adjusted such that the gap 50 between the bearing 66 at the extreme distal end of the first member 201 and the cartridge bung 44 is removed.

The assembly comprises a nut at its distal end, through which the lead screw may be screwed. It should be noted at this point that the dose member 28 and the nut 64 are fixed in rotation relative to the body 16 and the nut 64 is also fixed axially relative to the body 16. When the dose member 28 is in the position as shown in FIG. 4a, the relative interconnections between the components are provided such that the second member 22 is also held in fixed rotational position relative to the body 16.

The dose member 28 is first displaced in the distal direction 12 until it engages its stop face 19 at the nut 64. Thereby, all mechanical tolerances are taken up. The adjustment member 24 is then rotated relative to the dose member 28. This action rotates the proximal part 202 of the first member and the distal part 201 of the first member. Thereby the distal part 201 of the first member is advanced through the thread 31 at the second member 22 until the bearing 66 contacts the cartridge bung 44.

This abutment can be detected, for example by a strain gauge. The adjustment member 24 is then pushed in distal direction onto the detent 29 on the dose member 28. This action engages two sets of spline features 68 between the parts, thus locking them to prevent relative rotation.

Figure 4B:
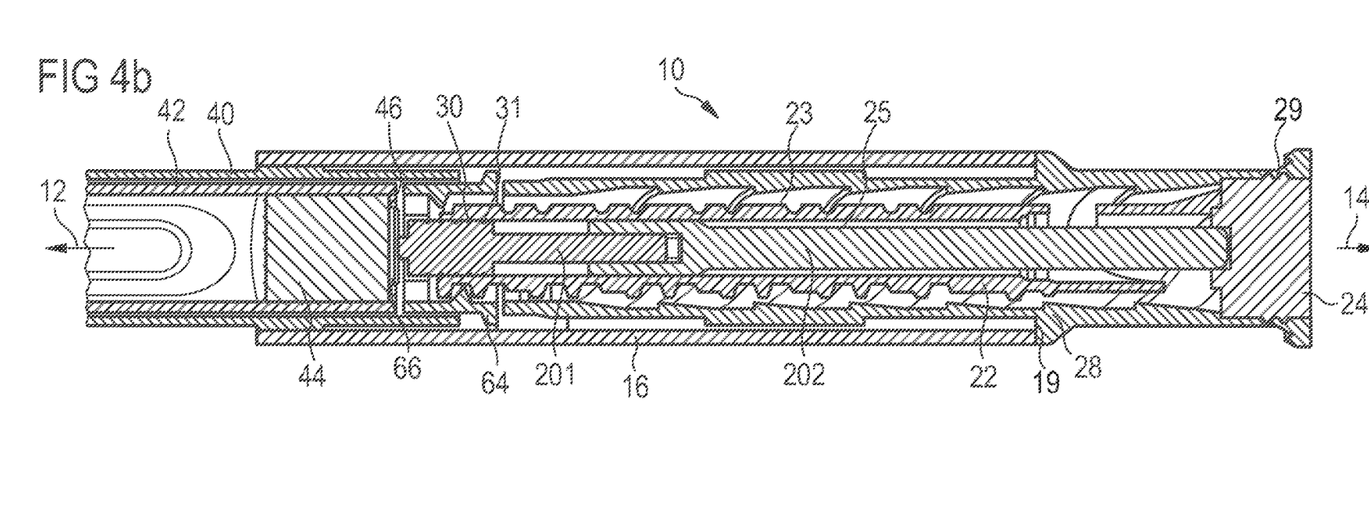
FIG. 4b shows a section view after adjusting the drug delivery device, wherein the drug delivery device comprises a second member and the second member comprises a lead screw.

When the adjustment member 24 is pushed in distal direction 12, this in turn displaces the proximal part 202 of the first member, engaging it onto a detent on the second member 22, which is not explicitly shown. This secondary action engages the two sets of spline 69 features between the proximal part 201 of the first member and the second member 22, thus locking them to prevent relative rotation. This state is shown in FIG. 4b.

Because the aperture of the proximal part 202 of the first member remains engaged with the part comprising the non-circular cross section on the distal part 201 of the first member, the distal part 201 of the first member is now locked in position relative to the second member 22. During use, the first member, the second member 22 and the bearing 66 are advanced by interaction with the dose member 28 and the nut 64 to displace the cartridge bung 44 and deliver doses of a fluid medicinal product.

The present examples and embodiments are to be considered as illustrative and not restrictive, and the invention is not to be limited to the details given herein, but may be modified within the scope and equivalence of the appended claims.

The invention claimed is:

1. An assembly forming a piston rod for advancing a cartridge bung in a drug delivery device, the piston rod comprising:
 a first member; and
 a second member, where the first member and second member are moveably connected to each other along a common longitudinal axis to define a first length that is equal to a sum of a length of the second member plus a length of the first member that extends beyond the distal end of the second member when the piston rod is in a first state, wherein when the piston rod is in the first state the second member does not move axially and the first member is axially moveable along the longitudinal axis with respect to the second member so that the first length of the piston rod can be increased to a fixed length and wherein when the piston rod is in a second state the extension of the first member beyond the distal end of the second member is greater than in the first state and the first member is locked in axial position with respect to the second member in order to define the fixed length of the piston rod, where the locked position forms a rigid connection through threaded engagement between the first member and the second member such that the fixed length of the piston rod does not change when a dose of a fluid medicinal product is set and then dispensed.

2. An assembly according to claim 1, wherein in the first state the first member is coupled to an adjustment member such that relative axial movement between the first member and the adjustment member is permitted and rotational movement relative to each other is prevented.

3. An assembly according to claim 1, wherein the assembly comprises a threaded engagement between the first member and the second member.

4. An assembly according to claim 3, wherein the threaded engagement is self-locking.

5. An assembly according to claim 1, wherein the first member is at least partly arranged inside the second member.

6. An assembly according to claim 2, wherein the adjustment member is arranged such that a rotational movement of the adjustment member relative to the second member advances the first member relative to the second member.

7. An assembly according to claim 6, wherein the first member comprises a pad configured to abut an assembled cartridge bung while being advanced relative to the second member.

8. An assembly according to claim 7, wherein the assembly comprises a means to detect the abutment of the pad upon the bung and to stop the movement of the first member.

9. An assembly according to claim 1, wherein in the second state of the assembly the first member and the second member are suitable for moving the cartridge bung into an assembled cartridge for dispensing a fluid medicinal product.

10. An assembly according to claim 2, wherein the adjustment member is located at a proximal end of the assembly.

11. An assembly according to claim 2, wherein in the second state of the assembly the adjustment member is locked with the second member in order to prevent rotational and axial movement with respect to the second member.

12. An assembly according to claim 2, wherein in the second state of the assembly the adjustment member is connected to the first member such that relative rotation and axial displacement between the adjustment member and the first member is prevented.

13. An assembly forming a piston rod for advancing a cartridge bung in a drug delivery device, the piston rod comprising:

an adjustment member comprising an aperture;

a first member operatively engaged with the adjustment member such that the first member extends through the aperture and can move axially relative to the adjustment member when the piston rod is in a first state; and a second member, where the first member and second member are axially and moveably connected to each other along a common longitudinal axis and through the adjustment member to define a first length when the piston rod is in the first state, wherein when the piston rod is in the first state the second member does not move axially and the first member is axially moveable with respect to the second member as a result of movement of the adjustment member so that the first length of the piston rod can be increased to a fixed length, and wherein when the piston rod is in a second state, the first member is locked in position with respect to the second member in order to define the fixed length of the piston rod, where the locked position forms a rigid connection through threaded engagement between the first member and the second member such that the fixed length of the piston rod does not change when a dose of a fluid medicinal product is set and then dispensed; and the adjustment member is locked with the second member in order to prevent rotational and axial movement with respect to the second member.

* * * * *